United States Patent
Chang et al.

(10) Patent No.: US 10,557,820 B2
(45) Date of Patent: Feb. 11, 2020

(54) METHODS AND APPARATUS FOR NANOMEMBRANE-BASED NUCLEIC ACID SENSING PLATFORM FOR PORTABLE DIAGNOSTICS

(71) Applicant: University of Notre Dame du Lac, Notre Dame, IN (US)

(72) Inventors: Hsueh-Chia Chang, Granger, IN (US); Zdenek Slouka, South Bend, IN (US); Satyajyoti Senapati, Mishawaka, IN (US); Li-Jing Cheng, Granger, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 313 days.

(21) Appl. No.: 15/043,401

(22) Filed: Feb. 12, 2016

(65) Prior Publication Data

US 2016/0238556 A1    Aug. 18, 2016

Related U.S. Application Data

(63) Continuation of application No. 13/476,783, filed on May 21, 2012, now abandoned.

(60) Provisional application No. 61/519,331, filed on May 20, 2011.

(51) Int. Cl.
*G01N 27/447* (2006.01)
*G01N 27/414* (2006.01)
*B82Y 30/00* (2011.01)

(52) U.S. Cl.
CPC ... *G01N 27/44704* (2013.01); *G01N 27/4146* (2013.01); *B82Y 30/00* (2013.01)

(58) Field of Classification Search
CPC ............ G01N 27/44704; G01N 27/3278
See application file for complete search history.

(56) References Cited

U.S. PATENT DOCUMENTS

| | | | |
|---|---|---|---|
| 4,661,224 | A | 4/1987 | Goldstein et al. |
| 6,893,816 | B1 | 5/2005 | Beattie |
| 2008/0257811 | A1 | 10/2008 | Peterman et al. |
| 2009/0242406 | A1 | 10/2009 | Han et al. |

OTHER PUBLICATIONS

Slouka, et al. (Langmuir, 2013, 29, 8275-8283) (Year: 2013).*

(Continued)

*Primary Examiner* — Gurpreet Kaur
*Assistant Examiner* — Steven E Rosenwald
(74) *Attorney, Agent, or Firm* — Knobbe, Martens, Olson & Bear LLP

(57) ABSTRACT

A DNA/RNA detection technology is provided. The open flow detection technique includes a substrate defining a pair of opposing microchannels, a pair of opposing electrodes in the opposing microchannels, and at least one ion exchanging nanomembrane coupled between the opposing microchannels such that the opposing microchannels are connected to each other only through the nanomembrane, wherein the nanomembrane is functionalized with a probe complementary to the macromolecule. A voltammeter is provided to measure the electrical current or potential across the nanomembrane, and detect a change in the measured electrical current or potential to quantify the presence of the macromolecule.

10 Claims, 13 Drawing Sheets

(56) References Cited

OTHER PUBLICATIONS

Senapati et al. (Top Curr Chem, 2011, 304; 153-169) (Year: 2011).*
Calibration and maintenance of Orion 3 Star pH meter (Year: 2010).*
Senapati et al., "A Nanomembrane-Based Nucleic Acid Sensing Platform for Portable Diagnostics," Top Curr Chem, 2011, 304, 153-160, published online Apr. 27, 2011.
Park et al., "An approach to fouling characterization of an ion-exchange membrane using current-voltage relation and electrical impedance spectroscopy," J. Coll. and Interface Sci., 294, 2007, 129-138.
Liu et al., "Capillar-valve-based fabrication of ion-selective membrane junction for electrokinetic sample preconcentration in PDMS chip," Lab Chip, 2010, 10, 1485-1490.
Frtiz et al., "Electronic detection of DNA by its intrinsic molecular charge," PNAS, Oct. 29, 2012, vol. 99, No. 22, pp. 14142-14146.

\* cited by examiner

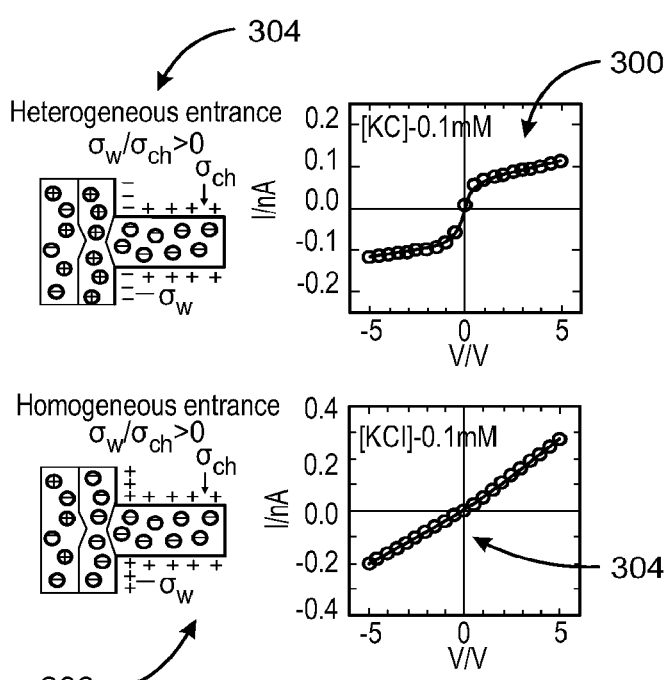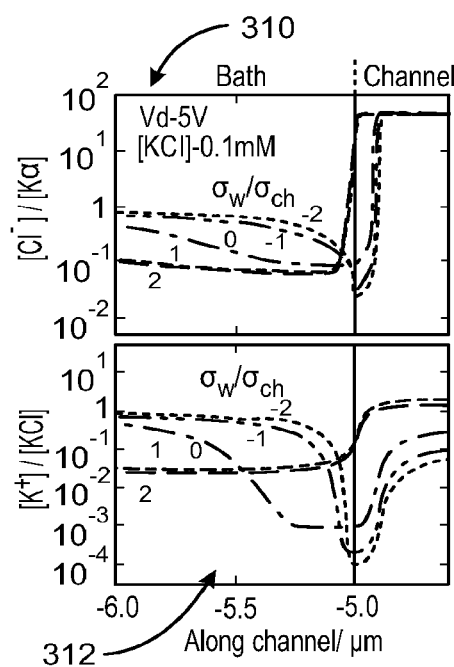
FIG. 3A
FIG. 3B
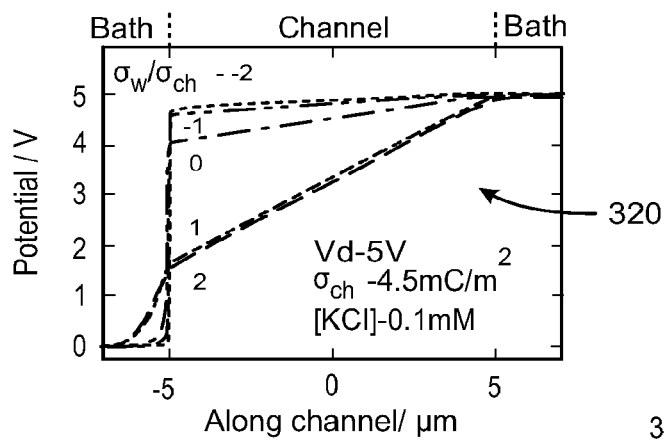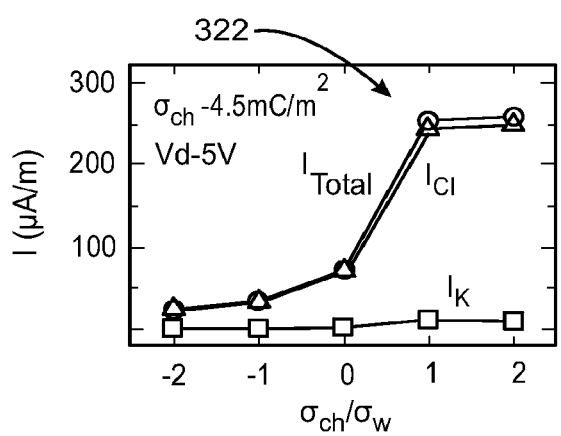
FIG. 3C
FIG. 3D

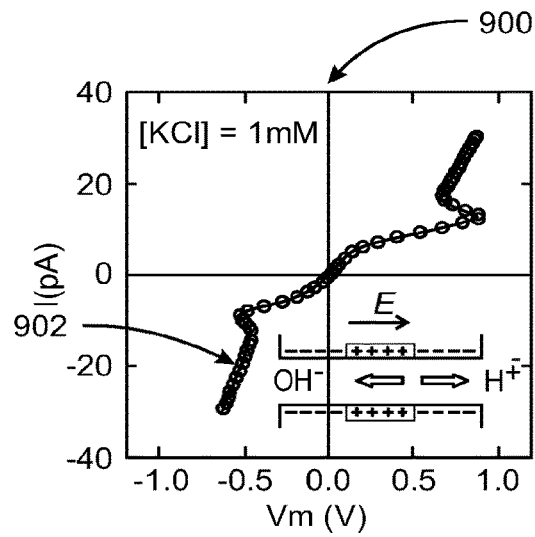
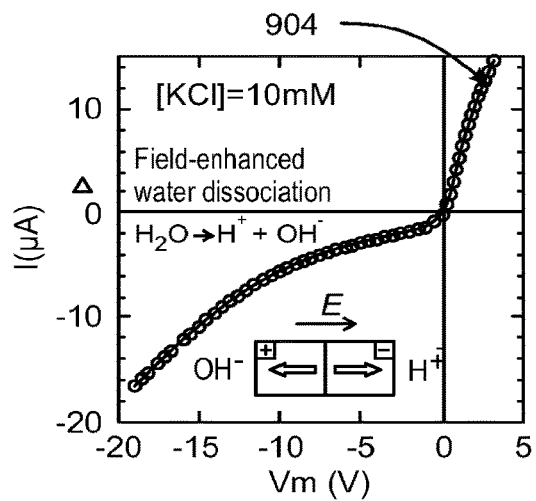
FIG. 9A    FIG. 9B
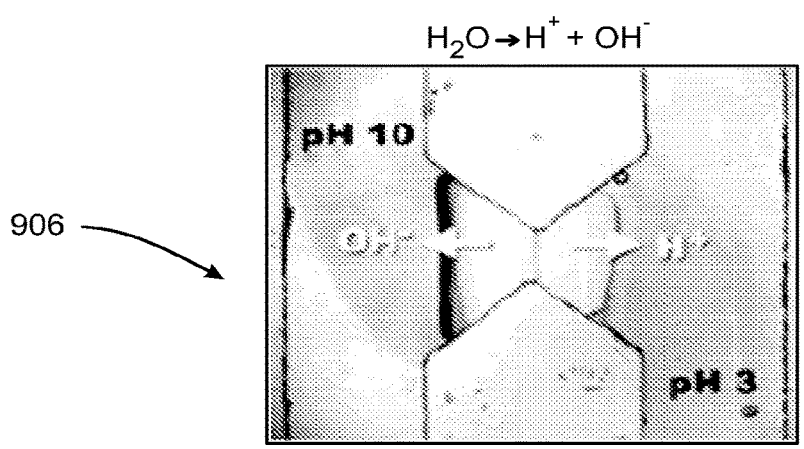
FIG. 9C

METHODS AND APPARATUS FOR NANOMEMBRANE-BASED NUCLEIC ACID SENSING PLATFORM FOR PORTABLE DIAGNOSTICS

CROSS-REFERENCE TO RELATED APPLICATIONS

This application is a continuation of U.S. application Ser. No. 13/476,783 filed May 21, 2012, which claims priority from U.S. Provisional Application Ser. No. 61/519,331, filed May 20, 2011, entitled "Electrokinetic Membrane Biosensor," the disclosures of which are incorporated herein by reference in their entireties.

This application is also related to International Patent Application No. PCT/US10/55679 entitled "Microchamber Electrochemical Cell Having a Nanoslot," filed Nov. 5, 2010, the contents of which are incorporated herein by reference in their entirety.

GOVERNMENT LICENSE RIGHTS

This invention was made with government support under NSF EFRI0937997 awarded by the National Science Foundation (NSF). The government has certain rights in the invention.

FIELD OF THE DISCLOSURE

The present description relates generally to microfluidic sensing technology and more particularly to methods and apparatus for nanomembrane-based nucleic acid sensing platform for portable diagnostics.

BACKGROUND OF RELATED ART

The development of rapid, portable, cheap, and/or easy-to-use detection devices for point-of-care application is oftentimes a challenge for the modern medical diagnostic industry to effectively diagnosis any number of diseases, including diseases that result in deaths of millions each year in developing countries. For example, conventional laboratory based technology, such as microarray, reverse transcription polymerase chain reaction (RT-PCR), etc. is relatively slow, employs multistep procedures, and/or uses bulky, expensive fluorescent detection units operated by trained technician. The cumbersome equipment requirements typically restrict the usage of such systems to the laboratory settings. The present disclosure provides for a nanomembrane based electrochemical nucleic acid detection platform that can be turned into a hand-held, portable device operated by workers with minimal instruction.

Rapid and portable devices for point-of-care application would allow for recognition of contamination and effective diagnosis of diseases that result in the deaths of millions each year in developing countries. The main challenges for the platform have been the elimination of sophisticated instruments and reagents, reduction in size to allow portability, acceptable detection sensitivity and robustness towards field sample variability, and sufficiently high assay rapidity to be compatible with portability. Presently, the genetic identification is mostly achieved by Enzyme-linked immunosorbent assay (ELISA), microarrays, and/or by real-time polymerase chain reaction (PCR). As previously noted, however, these conventional laboratory based technologies are relatively slow, employ multistep procedures, and use bulky and expensive fluorescent detection units operated by trained technicians. The cumbersome equipment requirements restrict the usage of such systems to the laboratory settings. Recent progress in dip-stick ELISA type assay is intended to circumvent the instrumentation and personnel demands, but its sensitivity remains unacceptable for field employment.

Electrochemical sensing with molecular probes functionalized onto the electrode sensor has also been developed as a candidate for label-free detection, particularly those that link the probe to the electrode with a linker that can enhance the electron transfer rate to the electrode once the target DNA has hybridized onto the probe. However, such self-assembled layer sensors remain unstable and hence not currently robust to the sample variability. Another label-free sensor technology that has been developed is the DNA chip technology which uses capacitance and field-effect transistor (FET) structures. Both techniques rely on the detection of the charges brought to the sensor surface by the hybridized target DNA. However, a recent survey has found that only DNA charges within the Debye electric double layer on the sensor can produce a capacitance or field-effect transistor signal. As the Debye layer is only a few nm thick under most practical conditions, there is a limit to the sensitivity of such capacitance and FET sensors, typically nano-molar. There is also a relatively significant fabrication cost typically associated with the capacitance and FET sensors. Electrochemical sensing and FET sensors all commonly suffer from long assay time as the hybridization reaction rate is limited by the diffusion of the molecules towards the probe, which can usually take hours for typical sample volumes.

As such, it is apparent that there is a need for an improved DNA/RNA detection technology. The present disclosure represents a new microfluidic technology that fully exploits the small spatial dimensions of a biochip and some new phenomena unique to the micro- and nanoscales. More specifically, the present disclosure addresses all the typical requisites for portable on-field applications: fast, small, sensitive, selective, robust, label- and reagent-free, economical to produce, and possibly PCR-free.

BRIEF DESCRIPTION OF THE DRAWINGS

FIGS. 3A-3D together are diagrams showing an example effect of entrance surface charge density and polarity on ion transport in a nanochannel.

FIGS. 9A-9C together illustrate an example field-enhanced water disassociation.

DETAILED DESCRIPTION

Figure 1:
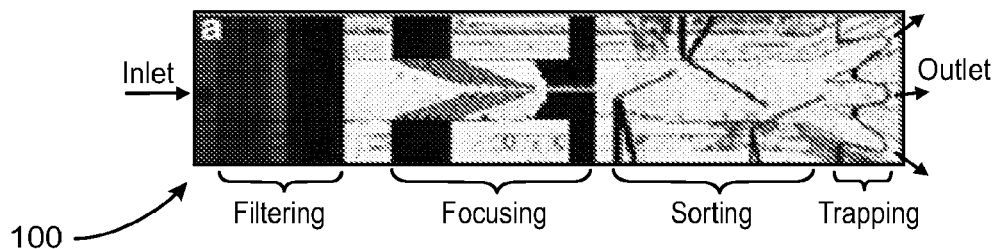
FIG. 1 is an illustration of an example open-flow DEP chip.

The following description of example methods and apparatus is not intended to limit the scope of the description to the precise form or forms detailed herein. Instead the following description is intended to be illustrative so that others may follow its teachings.

As noted above in the background, development of rapid and portable detection devices for point-of-care application is believed to be an important aspect of the modern diagnostics industry for effective detection of diseases in developing countries, from anti-terrorism and biowarfare applications to environmental monitoring, including the detection of harmful organisms on beaches. The most specific known sensing platform is currently the genetic detection platform, which identifies a particular sequence of the target pathogen's genome. As a result of active research in this area, small pretreatment units are now available that can concentrate the pathogens with membranes and beads, lyse cells, and remove chromosomal DNA for amplification in an integrated PCR chip. However, the key technological bottleneck remains the detection and quantification of the amplified DNAs.

Two known standards for genetic detection have appeared in the last decade, both involving labeling of fluorophores or quenchers onto the target molecule during PCR amplification: DNA microarray and real-time PCR. DNA microarrays offer sensitivity and large library volume. However, the assay time is long due to diffusion limitations. It also requires periodic rinsing to avoid nonspecific binding. Finally, the fluorescent confocal detection instrumentation is still too bulky and costly for portable applications. Quantification of the number of target DNAs is also impossible. Real-time PCR sacrifices large library volume for rapid and quantifiable detection, higher sensitivity, and good selectivity. However, it still requires bulky fluorescent detection instrumentation as well as expensive reagents. For instance, Model ViiATM7 available from Applied Biosystems is the size of a small refrigerator and can cost thousands of dollars. Thus, one challenge for portable diagnostics is then a miniature label-free nucleic acid sensing platform without any sophisticated instruments and reagents. The elimination of the PCR step would also be advantageous, as it would remove the 30-min thermal cycling time and the need for a PCR unit. In many medical applications, over a million DNA and RNA copies are available in a typical sample volume of 100 µL. Consequently, a detection platform capable of sensing one million copies of DNA/RNA can be PCR-free. For bacterial pathogens, each cell produces a million copies of mRNA and only one copy of DNA. However, the tradeoff for this relative abundance of RNA is its short life-time (typically less than an hour) due to rapid degradation. Hence, an RNA detection platform with an assay time of less than one hour (and without reverse-transcription PCR) would be the first known RNA detection platform of its kind.

Several label-free field-use DNA/RNA sensing technologies have been studied in the last decade. The most viable field-use sensing technology to date appears to be, electrochemical sensing. Electrochemical sensing with molecular probe functionalized electrode sensors can measure the change in electron-transfer rate upon docking of the target DNA/RNA molecules and redox reporter agents that can magnify this electrochemical current. Because many current carriers and inhibitors in the buffer can affect this electrochemical signal, even in the presence of surface-assembled monolayers, this sensing technology illustrates a lack of robustness and is oftentimes difficult to calibrate.

Capacitance, conductance, and FET electrode sensors have also attracted considerable interest recently. For such non-Faradaic sensors, excess charges brought to the surface by the docked DNA/RNA molecules and their associated potential can produce a local change in Debye double-layer conductance/capacitance and sub-surface current of the sensor. Conductance measurements are typically insensitive at practical ionic strengths because the presence of the DNA/RNA molecules in the high-conductivity Debye layer would not significantly affect the local conductance. Moreover, the same Debye layer is only a few nanometers thick for practical RNA samples, and only the lower fraction of the charges on the long (>10 kb) linear DNA/RNA is responsible for the capacitance signal, again resulting in low sensitivity. At its current state, conductance/capacitance/FET sensors have a detection limit higher than nanomolar, which translates into approximately $10^8$ copies of nucleic acid molecules for practical sample volumes, which is too high for field-based detection. Additionally, another drawback of all electrode sensors is their long assay time. For instance, at the low target molecule concentrations (picomolar) of practical samples, the diffusion time of long (more than kilobase) nucleic acids to the electrode sensor often exceeds hours, thus rendering such a platform ineffective for rapidly degrading RNA.

Several techniques have been previously suggested for removing the slow transport of long nucleic acid molecules to the electrode sensor. One known technique involves the activation of a high voltage at the electrode sensor to electrophoretically attract nearby DNAs. However, this electrophoretic concentration technique is highly nonspecific and other like-charge molecules can also be attracted to the sensor. Moreover, for buffers of high ionic strength, the elevated voltage can produce undesirable Faradaic reactions that can produce false current or voltage signals. Internal vortices, generated on microelectrodes by various ingenious but unreliable mechanisms, have also been suggested as a means of concentrating the target molecules towards the sensor. Generation of internal vortices remains, however, an imperfect science. It would be more desirable for the sensor to generate such vortices automatically at a precise location and for the vortices to exhibit a strong electric signal such that they can be detected and automatically controlled, this new technology will be described hereinbelow.

The present disclosure for portable DNA/RNA diagnostics includes a label-free electrode sensor that at least reduces diffusion limitation (i.e., short assay time), is relatively highly selective and sensitive, and yet is relatively insensitive to buffer ionic strength and chemical composition. The disclosed example ion-selective membrane sensor technologies, with properly tuned electrokinetic features and dynamic feedback actuation, address these specifications.

The applicants have recently developed an on-chip sol-gel silica fabrication technique and a nanocolloid assembly technique for on-chip membrane synthesis. Additionally, the applicants have also applied several photocuring polystyrene sulfonate or polyallylamine synthesis techniques to fabricate on-chip membranes. Still further, as described in International Patent Application No. PCT/US10/55679, the applicants have developed the technology to fabricate nanoslots on chips, which behave like single-pore membranes, for application in diagnostic chips. The membranes are used for molecular detection and involve continuous pumping of the sample solution in a cross-flow (tangential to the membrane surface) format to minimize hydrodynamic resistance. On-chip electrodes control the ionic current and voltage drop across these membrane components to produce the desired phenomena for rapid molecular concentration, transport, and detection.

Turning now to FIG. 1, an example integrated chip 100 for rapid detection of kilobase DNA with probe-functionalized nanocolloid assemblies is shown. The example integrated chip 100 is passive, not automated, and does not involve feedback control because the example chip 100 does not include several sensors and activation components that the present applicants have developed. In this example, the chip 100 is an open-flow disposable electrochemical printed (DEP) chip through which nanocolloids functionalized with complementary oligonucleotides are pumped. The example chip 100 includes an inlet, a filter, a focuser, a sorter, a trapper, and an outlet. In one example, a larger colloid (500 nm) with a long oligonucleotide is focused, sorted, and assembled passively at a microelectrode gate with symmetric and aligned top-down electrode pairs. The trapping of nanocolloids occur within a micrometer-sized region, and DNA solutions, ranging from picomolar to nanomolar concentrations, are then pumped over the nanocolloid assembly (membrane). A fluorescent imaging method may be used to quantify the specificity and concentration factor, whereas label-free detection yields quantifiable electrical signals.

One example solution to the robustness issue is to deplete the inhibitors and chemicals around the sensor such that close to deionized water conditions are always produced near the sensor, regardless of the buffer ionic strength and composition. In laboratory testing, several of these depletion technologies have been developed based on fabricated ion-selective nanoslots and on-chip nanoporous membranes. Significant counterion transport can rapidly deplete the counterions on one side of the membrane. To sustain electroneutrality, the co-ions also deplete rapidly to produce an ion-depleted zone. Sufficiently high DC fields (>100 V/cm) can deionize a 100 mm neighborhood (the depletion zone) near the membrane. The depletion layer with low interfacial ionic strength produces the maximum possible ion current without convection and exhibits a distinct limiting-current plateau in the polarization I-V or cyclic voltammetry spectrum as illustrated in the plot 200 shown in FIG. 2A. This nonlinear I-V polarization plot 200 is not due to electron-transfer reactions but bulk-to-membrane ion flux across the extended and depleted interfacial double layer. Its sensitivity to the interfacial charge in the depleted double layer allows sensitive conduction/capacitance detection of hybridization with the same actuation on-chip electrodes that drive the ion current.

At another critical voltage region shown in the plot 200, the limiting current gives way to a sharp increase in the current, the overlimiting current, which is a very sensitive signature of vortices driven by an extended polarized (Debye) layer at the membrane interface. Nonequilibrium (counter)ion transport across the ion-selective membrane produces an extended polarized layer and nonequilibrium over-potential that is orders of magnitude thicker/higher than the Debye screening length and the equilibrium zeta-potential. As such field-induced polarization is curvature- and perturbation-sensitive, the induced electro-osmotic flow is not uniform and the resulting backpressure can drive microvortices of specific dimension, and linear velocity at precise voltage windows. Such microvortices enhance the ion current through the membrane or nanoslot (hence the overlimiting current) and thus exhibit a sensitive polarization or single-sweep cyclic-voltammetry overlimiting signal as shown in the polarization curve (plot 200) in FIG. 2A. This strong conductance signature allows us to develop a smart platform that can generate such vortices on demand. Concentration of the charged dye by five orders of magnitude, as illustrated in FIG. 2B by the plot 210, is mostly due to convective concentration of the molecules at the stagnation points of the vortices. Other than the distinctive conductance signals of the membrane depletion/vortex phenomena, their actuation and sensing time is also very rapid. With thin membranes and short nanoslots as shown in FIG. 2A, the ion depletion and hydrodynamic timescales range from microseconds to seconds, allowing for rapid automation.

Figure 2A:
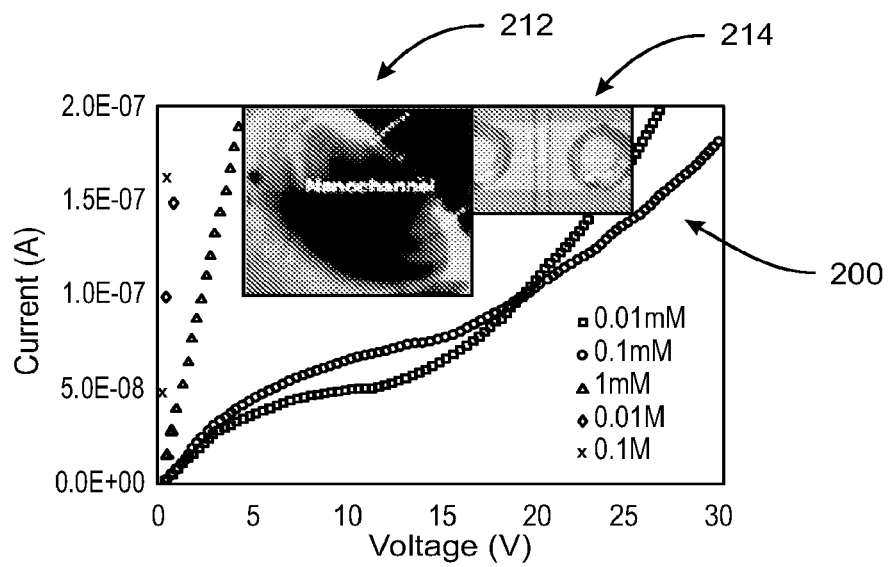
FIG. 2A is an illustration of an example enrichment and depletion across a nanoporous silica granule.
Figure 2B:
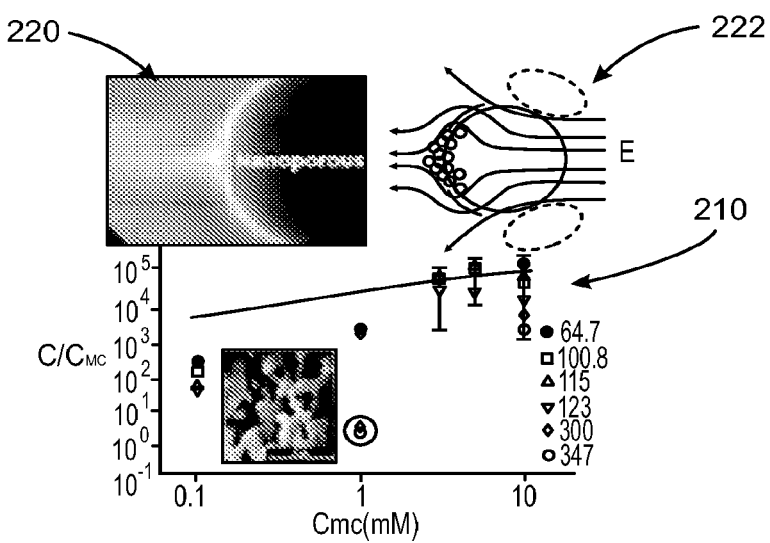
FIG. 2B is an example plot showing the depletion of charged fluorescent dye between two microreservoirs.

Specifically, FIG. 2A illustrates the depletion of charged fluorescent dye 212 at one entrance of a 50 nm nanoslot between two circular microreservoirs 214. The depletion has a very distinct polarization signature: the current plateaus at a limiting current value when depletion occurs. When vortices are observed in both the silica granule and the nanoslot beyond a critical voltage, the polarization (single-sweep cyclic voltammetry) curve shows a large overlimiting current beyond the limiting current plateau. The plot 200 shows the polarization characteristics of the nanoslot for different ionic concentrations of solution. Linear polarization curves missing the limiting region can be observed for concentrations above 0.1 mM. The disappearance of the limiting region is given by the loss of the ion-selective properties of the nanochannel as a result of decreasing Debye layer thickness inside the nanochannel.

As illustrated in FIG. 2B, enrichment and depletion across a nanoporous silica granule synthesized within a glass chip by sol-gel chemistry, produces a five orders of magnitude concentration of ions on one side of the granule and a comparable degree of ion depletion on the other side. More particularly, an example high magnification SEM image 220 of a silica granule with superimposed plot showing ion concentration is shown. Meanwhile, a schematic illustration of counterion movement 222 is also shown. Examination of the plot 210 illustrates that the concentration factor c/c1 as a function of the ionic concentration (c1) of the fluorescent solution for different sizes of silica beads.

Turning now to FIGS. 3A-3D, as can be seen, the ion current across an ion-selective medium can be very sensitive to the charge polarity and density on the surface outside the medium. For example, as illustrated in FIG. 3A, alumina nanochannels demonstrate that with negatively charged $SiO_2$ entrance side-walls, the ion conductance across the positive-charged $Al_2O_3$ nanochannel is suppressed and shows a nonlinear I-V characteristic at 300, 302. The ion charge inversion induced by the heterogeneous entrance charge enhances ion depletion as shown in FIG. 3B and hence creates a large voltage drop at the channel entrance as seen in FIG. 3C. The heterogeneous entrance charge efficiently suppresses the flow of counterions through the nanoslot (anions in the case of the positively charged $Al_2O_3$ nanochannel). This effect is clearly seen in FIG. 3D and is reflected in the measured I-V curves 300, 302 depicted in FIG. 3A. The ion conductance is found to change significantly when the surface charge of the entrance side-walls converts its polarity and density. The shift of ion conductance induced by surface charge conversion will be utilized as a basis of DNA/RNA sensing. Hybridization of DNA or RNA on a positively charged anion-selective medium can be detected by measuring the nonlinear I-V characteristics.

More particularly, FIG. 3A illustrates the effect of entrance surface charge density and polarity on the ion transport in a 20 nm thick, 60 mm long, positively charged $Al_2O_3$ nanochannel. In FIG. 3A, a heterogeneous nanochannel entrance 304 induces ion charge inversion at the channel access. A homogenous nanochannel entrance 306 is also shown. The charge of entrance side-walls, $\sigma_w$ and the charge of the nanochannel $\sigma_{ch}$ appear in opposite polarities, with $\sigma_w/\sigma_{ch}<0$. The figure also illustrates the experimental I-V characteristics of an $Al_2O_3$ nanochannel device with negatively charged silica entrance side-walls 300 and $Al_2O_3$ entrance side-walls 302 measured with 0.1 mM KCl. FIG. 3B illustrates the calculated Cl ion 310 and K ion 312 distributions near left channel entrance with values of $\sigma_w/\sigma_{ch}$ varying from 2 to −2. FIG. 3C illustrates the calculated potential profile 320 along the nanochannels with varied $\sigma_w/\sigma_{ch}$ ($\sigma_{ch}$=4.5 mC/m²) under $V_d$ (Voltage applied across the nanochannel)=5 V. FIG. 3D, meanwhile illustrates a summarized theoretical ion current density 322 (current per channel width) of the nanochannels with varied $\sigma_w/\sigma_{ch}$.

Another step is the proper development of surface chemistry to attach addressable probes onto different membrane sensors. In the disclosed example, this can be achieved by patterning UV-curable acrylic-based polymers inside the microfluidic channel doped with different monomers containing charged or functional groups. Such polymers may be ion-selective and provide reactive chemical groups on their surfaces for the attachment of DNA/RNA probes. The functionality of at least some of the example devices disclosed herein relies on the ion-selectivity of the polymeric material, which is less dependent on ionic strength than the nanofluidic counterparts. Briefly, using photolithographic techniques, cation- and anion-exchange membranes are defined in glass microfluidic channels by crosslinking positively charged diallyldimethylammonium (DADMA) and negatively charged 2-acrylamido-2-methyl-1-propanesulfonic acid (AMPSA) using a crosslinker (N, N'-methylene bisacrylamide) and photo-initiator. Each example membrane has a defined width and length of few tens to hundreds of micrometers, bridging two microfluidic channels that are about 20 mm deep and 20-100 mm wide. In one instance, the pore size of the nanoporous membrane can be controlled by varying the concentration of the monomers and crosslinker. To achieve surface functionalization of the oligo probes, the surface of an anion-exchange membrane is modified with amino groups by using allylamine as an additive in the prepolymer solution. The DNA or RNA probe (~27 bases) pre-attached with functional groups of choice can then be used to functionalize the probes onto membrane surface. Through examination by microscope and measurement of the ability to deplete ions, the polymerization time and the concentrations of crosslinker and photo-initiator have been optimized to produce reproducible, well-defined ion-selective membranes with functional chemical groups inside microchannels.

Figure 4A:
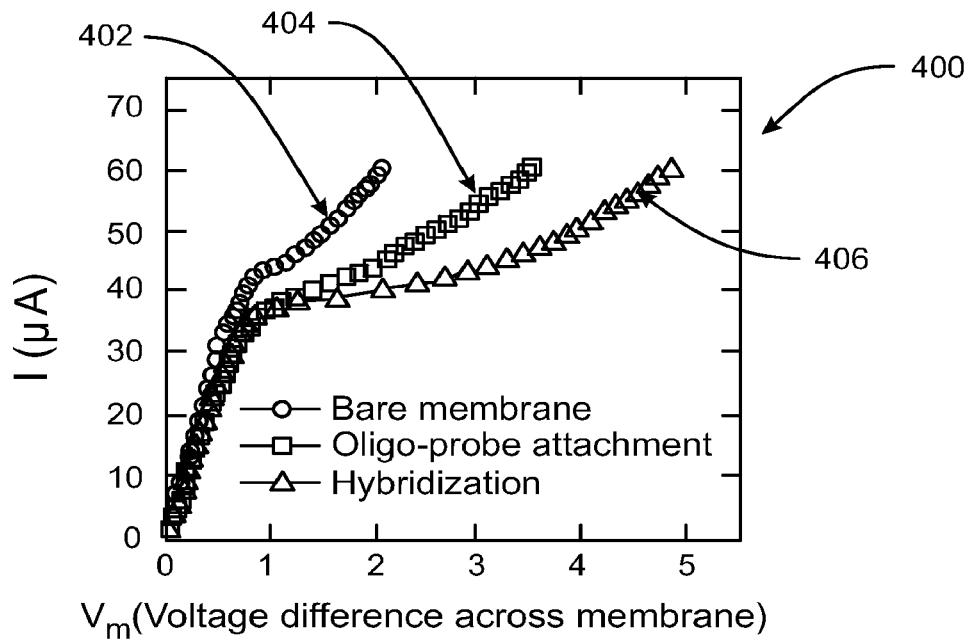
FIG. 4A is graph showing a current voltage (I-V) curve for an example device of FIG. 4B after hybridization.
Figure 4B:
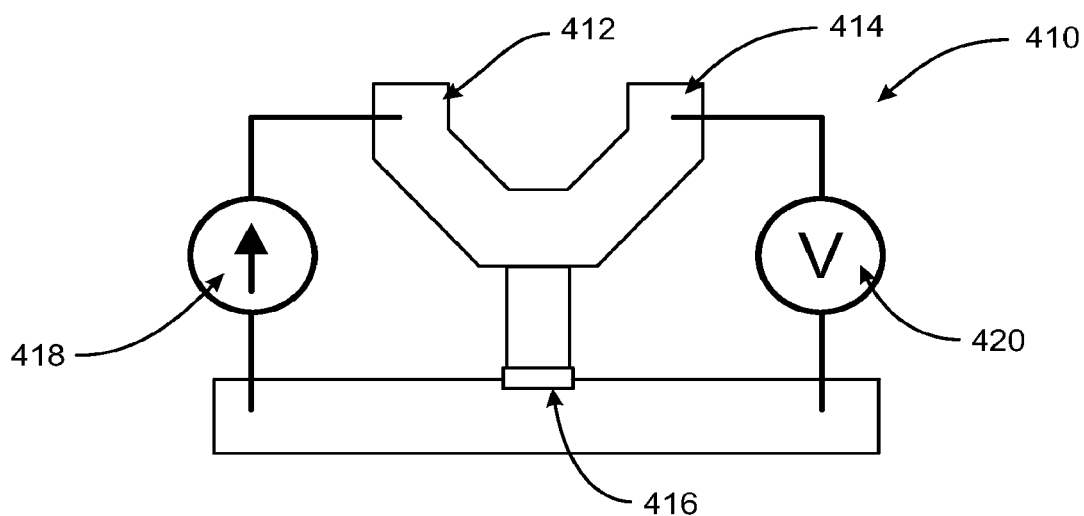
FIG. 4B is an example nanomembrane device constructed in accordance with the teachings of the present invention.
Figure 4C:
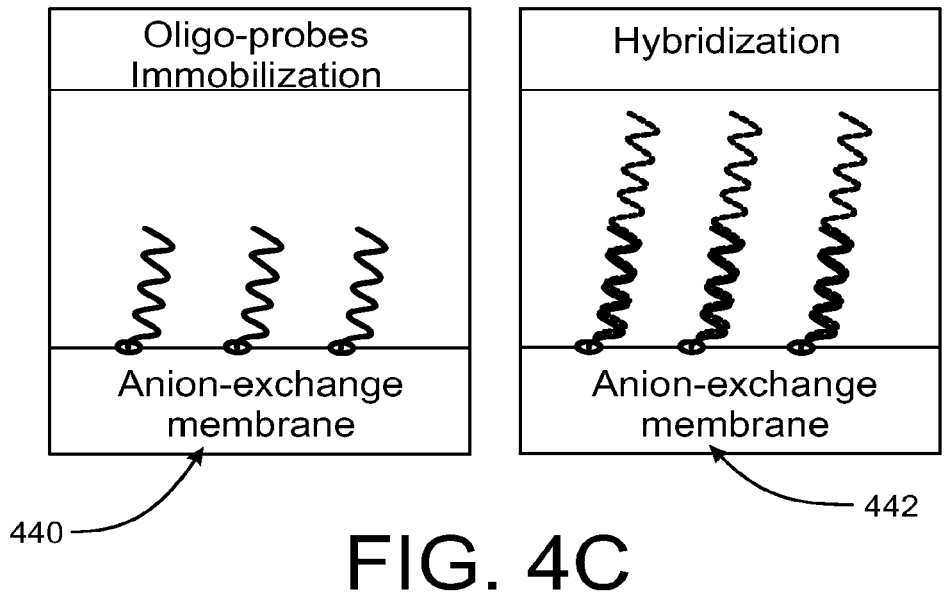
FIG. 4C is a schematic illustration of an example nucleic acid hybridization onto immobilized oligoprobes.

For example, turning to FIGS. 4A-4C, there is shown experimental evidence that the onset voltage and the onset of overlimiting current, features of the nonlinear I-V curve of our sensor, are sensitive to nucleic acid hybridization onto oligo probes functionalized onto the surface of the ion-selective medium, as the resulting change in the surface charge can enhance or eliminate the extended Debye layer. Specifically, FIG. 4A illustrates a plot 400 of a I-V curve of a bare membrane 402, an oligo probe attachment 404, and a hybridization 406. The voltage differential between the plots 402, 404, 406, is particularly large because of the nearly infinite differential resistance at the limiting current conditions. More particularly, significant change of I-V characteristics in the overlimiting current regime is observed after RNA hybridization from a picomolar sample. The 50% change in conductance is compared to typical 5% changes of electrochemical electrode sensors at the same concentration (low-voltage region). In contrast, the low-voltage linear ohmic region, where classical electrochemical sensors operate, registers an insignificant shift. Conveniently, the depleted and extended double layer, which can be three orders of magnitude thicker than the Debye layer, also allows more charges on the target RNA to contribute to the effective surface charge. If the membrane is oppositely charged from the hybridized or functionalized molecules, the latter can even invert the charge on the membrane surface, eliminating the overlimiting current substantially when the surface is effective electroneutral with exact compensation. The result is a very sensitive RNA sensor with picomolar sensitivity, compared to the nanomolar sensitivity of most electrode electrochemical sensors.

Referring to FIG. 4B, an example sensor 410 includes a plurality of microchannels 412, 414, and an oligo probe functionalized membrane 416. A current source 418 and a voltammeter 420 are also included, the operation of which is described in detail herein. As will be detailed further, the sensor 410 may include any number of microchannels including multiple pairs of microchannels. Additionally, as will be appreciated, the microchannels can each function as an inlet and/or outlet channel as desired. FIG. 4C, meanwhile illustrates the membrane 416 prior to hybridization 440 and post hybridization 442.

Dielectrophoresis (DEP), a molecular force due to induced molecular dipoles, has been shown to be an effective means of concentrating large DNA/RNA molecules into the depleted region near the membrane surface (see FIG. 4B) where the probes are functionalized. The electric field is focused by the nanopores in the membrane to produce a high field gradient at the membrane interface. A polarizable molecule in the bulk, with a large induced dipole, would then experience a net force towards the high-field region (the membrane surface). With the intense field amplification of nanopores, this DEP force on the molecules can overcome molecule-membrane repulsive interaction.

In one example fluorescent correlation spectroscopy (FCS) experiment this domination of dielectrophoretic attraction over like-charge repulsion with floating probe-functionalized carbon nanotubes (CNTs) and the fluorescently labeled kilobase target single-stranded DNA (ssDNA) was confirmed. Because CNTs quench the fluorophores on hybridization of target DNA, reduction in the fluorescent intensity can be used to quantify the hybridization degree and the attraction of the molecules to the nanoelectrode. As seen in the experimental setup of FIG. 5A, and the results of the experiment of FIG. 5B, an FCS detection experiment 500 of DNA hybridization from a picomolar solution is shown. The setup 500 includes a Detector 502, a Flourescence 504, a laser 506, an objective 508, and a flourescent quench of ssDNA 510.

Figure 5:
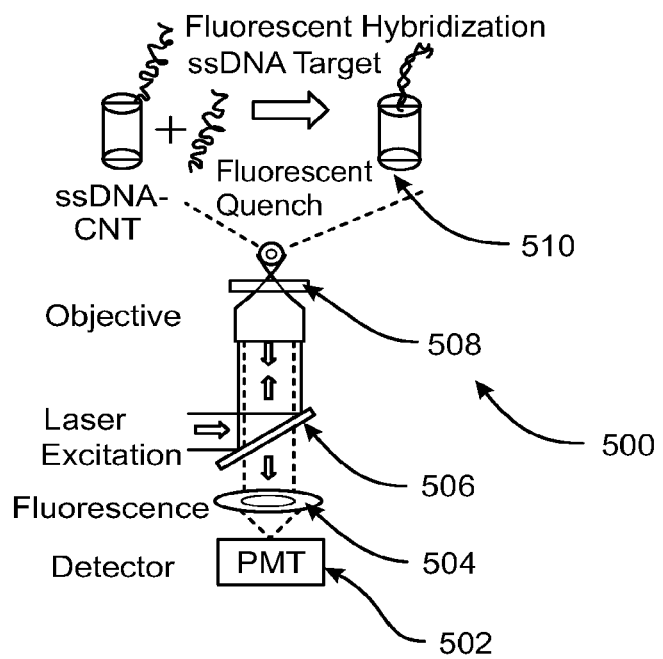
FIG. 5 is an illustration of an example device suitable for FCS detection of DNS hybridization.

As a result of the experimental setup 500, as shown in FIG. 5, dielectrophoretic attraction due to the field-focusing CNTs allows hybridization in less than 2 min at picomolar concentrations 520. In contrast, the diffusion time for the long ssDNA at this concentration is hours 522.

Instead of floating CNTs, one example system is able to utilize 50 nm nanoslots on glass (see FIG. 3B) and is able to show concentration of ssDNA to the nanoslot. This same DNA concentration is shown with the nanoporous membrane 416 in FIG. 4B, with a concentration factor of up to five orders of magnitude. Alternatively, 100 nm nanocolloids can be assembled into a nanocolloid crystal (e.g., a membrane) at a top-down electrode pair by nanocolloid DEP, such as shown in FIGS. 6A-6F. The 10 nm spacing between the nanocolloids focuses the electric field of the electrode gate and can rapidly (order of seconds) trap and concentrate ssDNA molecules of a Green Crab species from a picomolar solution onto the on-chip nanocolloid membrane by molecular DEP.

Figures 6A, 6B, 6C:
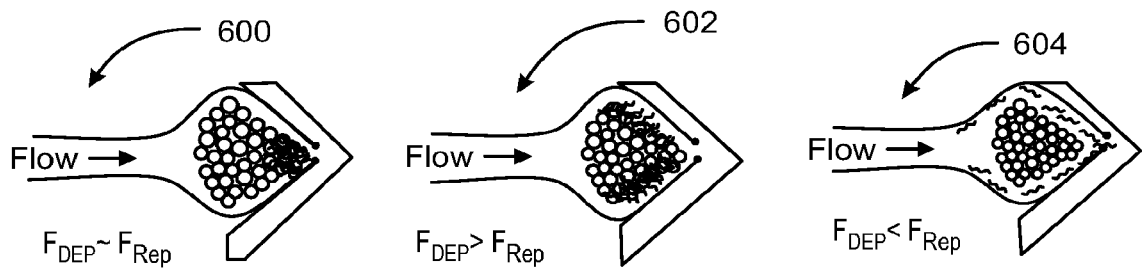
FIGS. 6A-6C together illustrate images of an example fluorescence of an example trapping electrode tip.

Specifically, as illustrated in FIG. 6A-6C, a properly tuned DEP force can drive the DNAs towards the nanostructure against electrostatic repulsion from the likecharged structures, but they will not deposit onto the surface until they are convected to a sharp tip (~10 μm) at the nanostructure, see FIG. 6A. More particularly, FIGS. 6A-6C illustrate a schematic of fluorescence images of the trapping electrode tip in FIG. 2A, showing the 100 nm nanocolloid assembly at fixed times after the Green Crab DNA solution had been injected but at different AC frequencies 600, 602, 604. For instance in the schematic 600, the chosen AC frequency causes the dielectrophretic force ($F_{DEP}$) to be approximately the same as the repulsive force ($F_{REP}$). In the schematic 602, the chosen AC frequency causes the dielectrophretic force ($F_{DEP}$) to be greater than the repulsive force ($F_{REP}$), and in the schematic 604, the chosen AC frequency causes the dielectrophretic force ($F_{DEP}$) to be less than the repulsive force ($F_{REP}$). In these examples, the fluorescence is detectable only when the ssDNA is concentrated beyond the micromolar level from the undetectable concentrations (nanomolar to picomolar) of the injected solution. Trapping at the assembly is achieved at low frequencies, whereas none occurs at high frequencies.

Figure 6D:
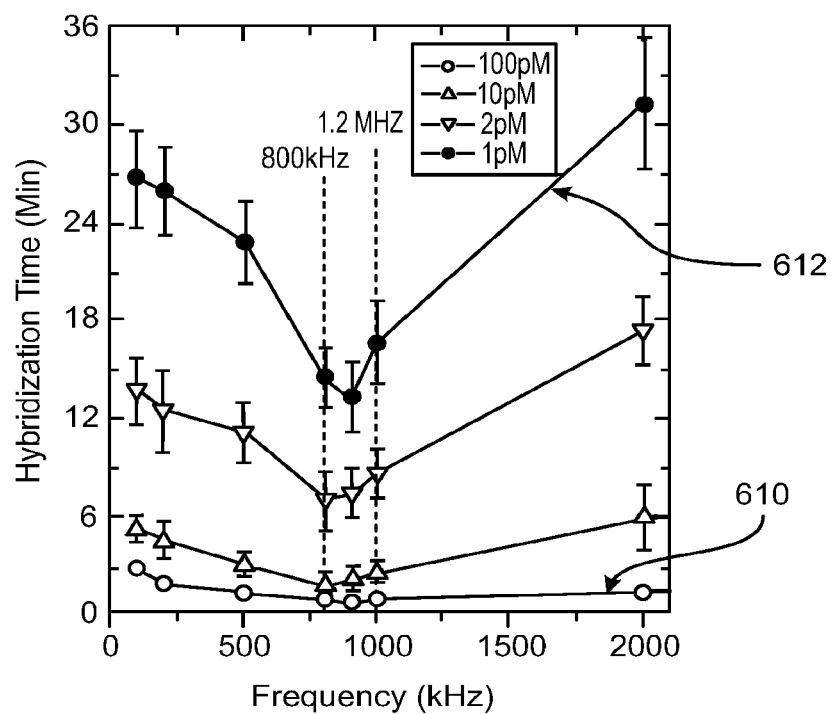
FIG. 6D is a graph showing an example plot of detection time with decreasing concentration.
Figure 6E:
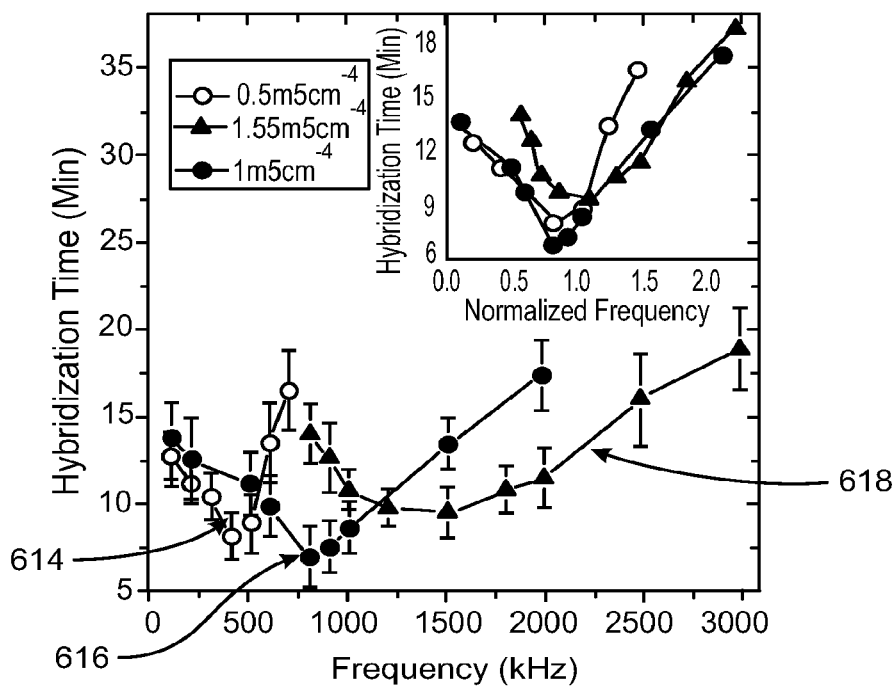
FIG. 6E is a graph showing an optimum frequency for a given electrolyte strength.
Figure 6F:
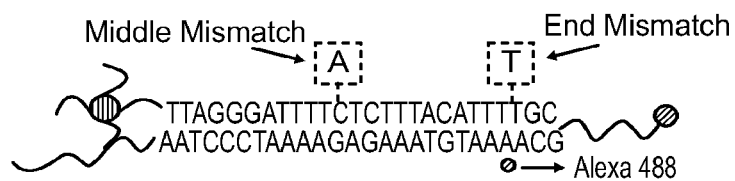
FIG. 6F is a graph showing fluorescence intensity from different example flow rates.
Figure 6F:
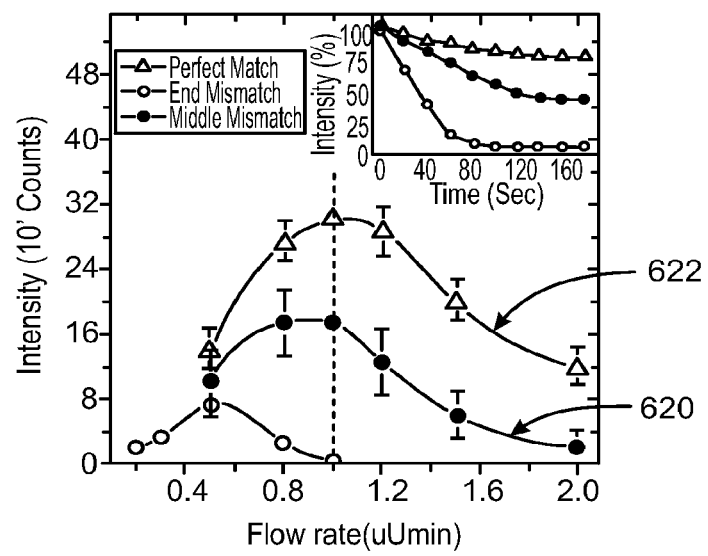

As can be seen from the plot in FIG. 6D, a detection time increases with decreasing concentration. Specifically, in this example, a 100 pM concentration 610 compared to a 1 pM concentration 612 demonstrates a dramatic time difference. Additionally, as can be seen in FIG. 6E, there is an optimum frequency for each electrolyte strength 614, 616, 618 with a sharp minimum in detection time, which scales as $D/\lambda^2$ where D is the molecular diffusivity of the molecule and λ is the Debye length for the given electrolyte strength. Referring to FIG. 6F, fluorescence intensity at 2 min from different flow rates of 100 pM of a 1 kb ssDNA target from a Green Crab species with a 26 base docking segment in the middle (620) and with a complementary 26 base oligo on the nanocolloid (622) or with a single end mismatch (624). The flow rate window with single-mismatch (624) discrimination is indicated by a vertical dashed line. The scheme above the plot of FIG. 6C shows the actual 26 base ssDNA docking sequence and the location of mismatched bases It will be appreciated by one of ordinary skill in the art that intermolecular interaction can be adjusted to minimize nonspecific binding. A concentration factor exceeding $10^5$ within minutes is observed from the fluorescent imaging in FIGS. 6A-6C thus rapidly and significantly enhancing the sensitivity of any sensor at the trapping location. The shear rate and AC frequency can be optimized so that the sensor can selectively discriminate against kilobase target molecules with a single mismatch in the 26 base pairing segment in the middle (FIG. 6F). This shear-enhanced selectivity eliminates the need for rinsing and washing steps.

Apart from dielectrophoretic concentration, which is not effective for small nucleic acids because the DEP force scales as the cubed power of the hydrodynamic radius of the molecule, the present disclosure successfully demonstrates rapid analyte preconcentration based on ion depletion at an ion-selective membrane in microfluidic chips. Ion depletion at the surface of a membrane establishes a conductivity gradient across the boundary of the ion-depleted region. When flux of charged analyte molecules (due to flow, electrophoresis or other particle forces) occurs across this boundary, the concentration gradient at the boundary produces an accumulation of the analyte molecule at the boundary of the depletion region.

Figure 7A:
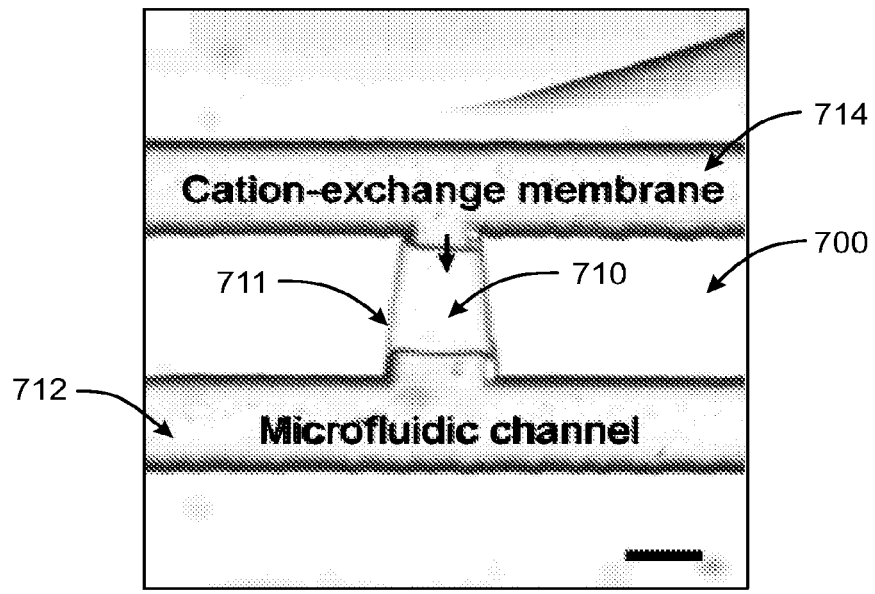
FIG. 7A is optical microscope image of an example pre-concentrator based on a charge-selective membrane.
Figure 7B:
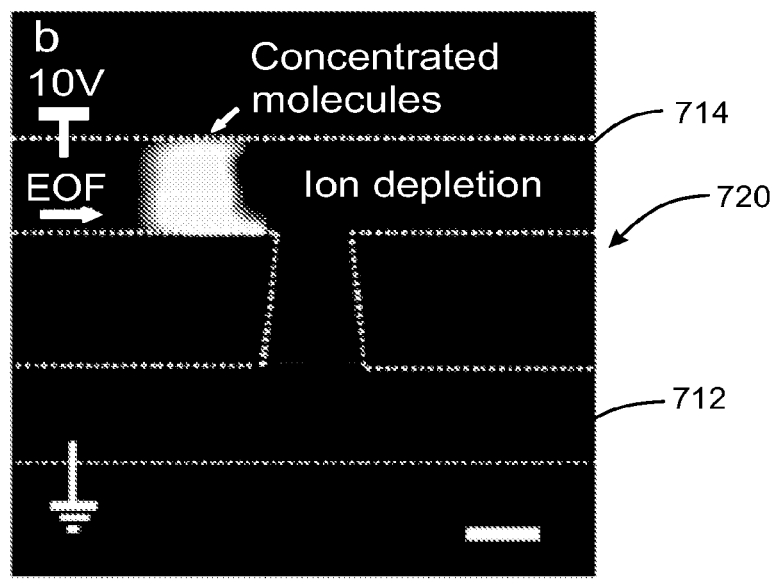
FIG. 7B is an illustration of an example electroosmotic flow of fluorescently labeled molecules in the device of FIG. 7A.

Referring now to FIG. 7A, a cation-exchange membrane 710 UV-polymerized in a microslot 711 bridging two microfluidic channels 712, 714 can induce deionization under voltage biases. The ion-depletion region functioning as an energy barrier traps the molecule passing across it in an electroosmotic flow tangential to the membrane 710 on the side. The example UV-curable ion-selective membrane 710 disclosed herein offers concentration efficiency and proccessability compared to the microfabricated nanochannels of the prior devices or Nafion resins. Unlike the 100 nm thick nanochannels and surface-patterned Nafion thin films, the example membrane slot 711 has the same depth as the microfluidic channels 712, 714, yielding a large junction area. The large cross-section area provides greater ion current and better control of iondepletion in the microchannels 712, 714. Therefore, preconcentration can be achieved in few seconds. The fluorescence image 720 in FIG. 7B shows the concentration of labeled molecules by several orders of magnitude in 10 s from a solution being pumped by electro-osmosis from the left to right in the top microfluidic channel 714, after 10 V is applied across the membrane 710. In particular, the image 720 shows a concentration of fluorescently labeled molecules taking place 10 s after applying a voltage bias of 10 V with a scale bar of 50 mm, wherein the microchannel 714 experiences electroosmotic flow (EOF). Moreover, the example membrane 710 adheres to acrylfunctionalized glass surfaces well. Although the current membranes are synthesized on glass chips to allow easy inspection and testing, the same technology can be transferred to hard polymer chips, which should be cheaper to produce and easier to bond.

The presence of the docked RNA/DNA and their mobile counterions produce a large conductivity change at the depleted region, which is where most of the voltage drop occurs. Moreover, the extended Debye (polarization) layer allows more of the charges on a long (>2 nm) DNA/RNA molecule to contribute to the charging capacitance and surface-charge compensation on the surface. As described earlier, the surface charge can sensitively alter the onset voltage for microvortices and the overlimiting currents that the vortices contribute to. These effects greatly enhance the capacitance, conductance, and polarization signatures of the docked nucleic acids, resulting in sensitive nonlinear I-V polarization signatures, such as those due to the charge-inversion after hybridization shown in FIG. 4A.

Figure 8A:
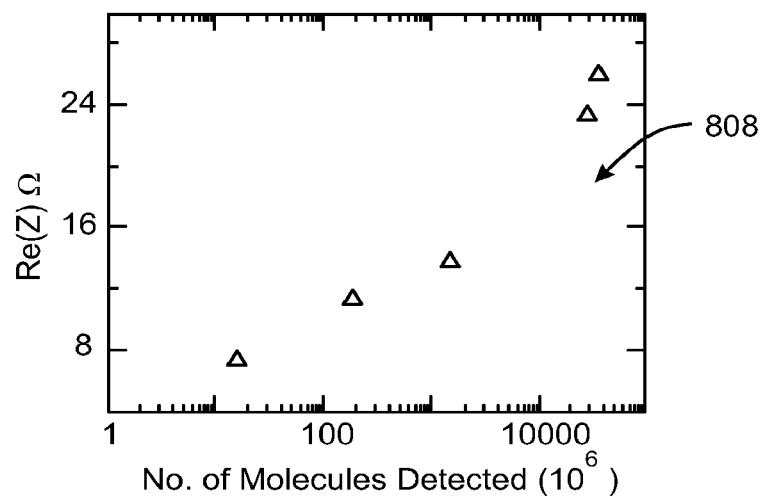
FIG. 8A is a graph showing the Warburg impedance spectrum of an example nanoslot.
Figure 8B:
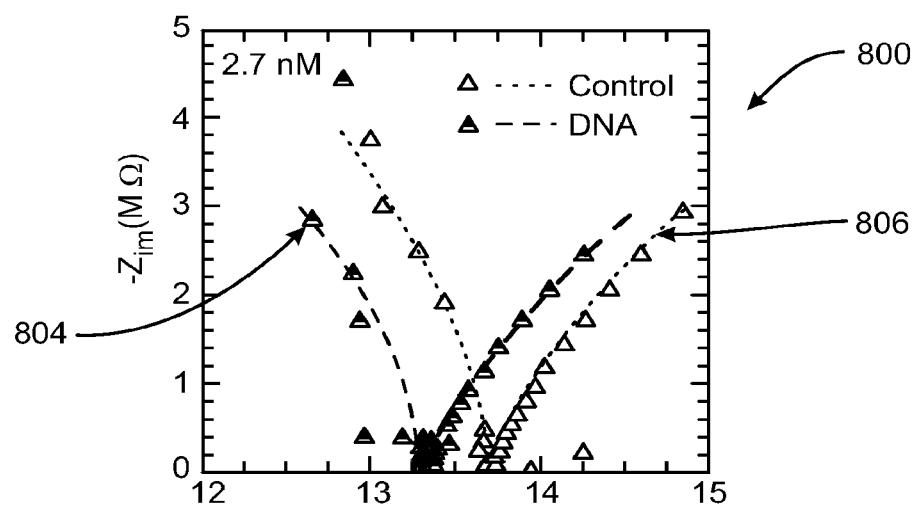
FIG. 8B is a graph showing a shift in the intercept allowing quantification of the number of target macromolecules in the microchannel.

The dynamics of depletion layer formation with strong charging also exhibits a distinct capacitance signature in the AC impedance spectrum, such as shown in FIG. 8B. A plot 800 of a Warburg spectrum has a constant phase angle of $\pi/4$, whose modulus increases with decreasing frequency and is classically associated with diffusion controlled ion transport. For instance, as shown in FIG. 8B, the warburg impedance spectrum 800 of the nanoslot illustrated in FIG. 2B, shows a shift to lower resistance with a 2.7 nM 1 kb E. coli ssDNA solution relative to the control without DNA. The identified shift in the intercept with the real axis between a 2.7 nM 1 kb E. coli ssDNA solution 804 relative to the control without DNA 806 allows precise quantification of the number of ssDNA molecules 808 in the microreservoir down to $10^7$ copies (FIG. 8A).

It will be appreciate that under an AC field, the depletion region next to a membrane sensor is created periodically during the half-cycle when the mobile counterions are driven into the nanoslot or on-chip membrane 711. The depletion layer dynamics was verified by high-speed confocal imaging to be a diffusive one such that its thickness grows in a self-similar manner as $\sqrt{Dt}$ and was shown to exhibit the Warburg spectrum, with a constant phase of $\pi/4$ (FIG. 8B). The intercept of the Warburg spectrum with the real axis represents the limiting ion flux when the depletion layer is smallest in dimension—just above the critical voltage where the depletion phenomenon can be sustained. It hence offers an accurate estimate of the low conductivity in this small region, as most of the voltage drop occurs there. As mentioned earlier, the presence of a few macroions attracted to this small depleted region by DEP can significantly change its local conductance. In FIG. 8B, there is illustrated sensitive detection of E. coli ssDNA below nanomolar concentrations or $10^7$ molecules. With a reduction of the nanoslot width, down to the micrometer size of the nanocolloid assembly in FIG. 6A, the detection limit can be expected to reach below picomolar concentrations or $10^5$ copies of nucleic acid.

The same Warburg signal can be captured with the field across the nanocolloid assembly of FIG. 6A to allow label-free quantification of the docked DNA/RNAs. This large-voltage AC impedance technique is quite distinct from the classical low-amplitude impedance spectroscopy for electron transfer rates because the current example induces nonequilibrium ion transport through the ion-selective nanoslot or membrane to produce extended polarized Debye layer and concentration depletion layers.

The single mismatch (SNP) discrimination capability of the device shown in FIG. 6F is due to hydrodynamic shear. It will be understood that shear is most discriminating because it can meter small thermal-energy-level hydrogen bond energies to dehybridize the target molecules. Microscale bipolar membrane technologies may be used to control the local pH in microfluidic chips to improve both the specificity and selectivity of the membrane sensor. These bipolar membranes/nanopores exhibit distinct hysteretic I-V polarization and cyclic voltammetry signatures due to local field-induced water-breaking reactions that generate more ions. An image 900 of the pH fronts generated by a UV-polymerized bipolar membrane composed of positively charged dimethylammonium and negatively charged sulfonic groups are shown in FIG. 9C. The ion currents can drastically increase when reversely biased at a high voltage, forming a breakdown regime. In accordance with the second Wien effect, the ionic current breakdown results from the enhanced water dissociation into cation ($H^+$) and anion ($OH^-$) at the bipolar junction, in which a strong electric field greater than 10 MV/cm can build up at a reverse bias. These membrane actuation components can be used to control the local pH for the example integrated devices disclosed herein, with feedback control based on the distinctive hysteretic polarization signals and I-V characteristics seen in FIGS. 9A and 9B, respectively.

More particularly, FIGS. 9A-9C illustrate that field-enhanced water dissociation increases ionic currents in a reverse-biased 20 nm thick bipolar-junction nanofluidic channel containing positive and negative surface charges (|Vm|>0.6 V) (plot 902 at FIG. 9A), and a UV-polymerized bipolar membrane (Vm<−10 V) (plot 904 at FIG. 9B). Still further, Hydroxide ions and protons are produced at the bipolar membrane junction and transport to opposite sides of the membrane as shown at FIG. 9C (906). The pH change of the solution in the microchannels can be observed with a mixture of universal pH indicator, wherein in the example illustrated, the left half of the bipolar membrane is positively charged whereas the right half is negatively charged.

Figure 10:
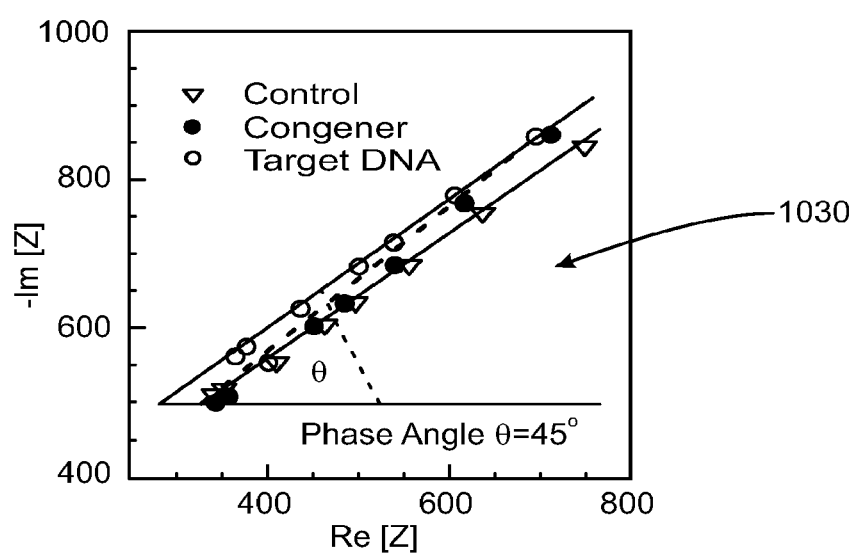
FIG. 10 is a graph showing the Warburg signal measured across the example membrane sensor assembly.

Integration of the example chips disclosed herein into the passive sensor chip 1000, may lead to an interrogated Warburg signal 1030 which may be seen illustrated in FIG. 10. The detection limit of the Warburg impedance signal is picomolar concentrations or about the desired $10^5$ copies, the detection time is about 15 min, and the selectivity is three mismatches in the 27 base pairing segments. The example device 1000 shows that long kilobase target ssDNA produces a larger signal, consistent with the extended Debye layer allowing more of the charges of a long molecule to contribute to the local charge capacitance and conductance. A sensor of the present invention is capable to differentiate a Green Crab species from a congener species with three mismatches over the 26 pair docking segment due to the hydrodynamic shear offered by the high through flow.

Figure 11:
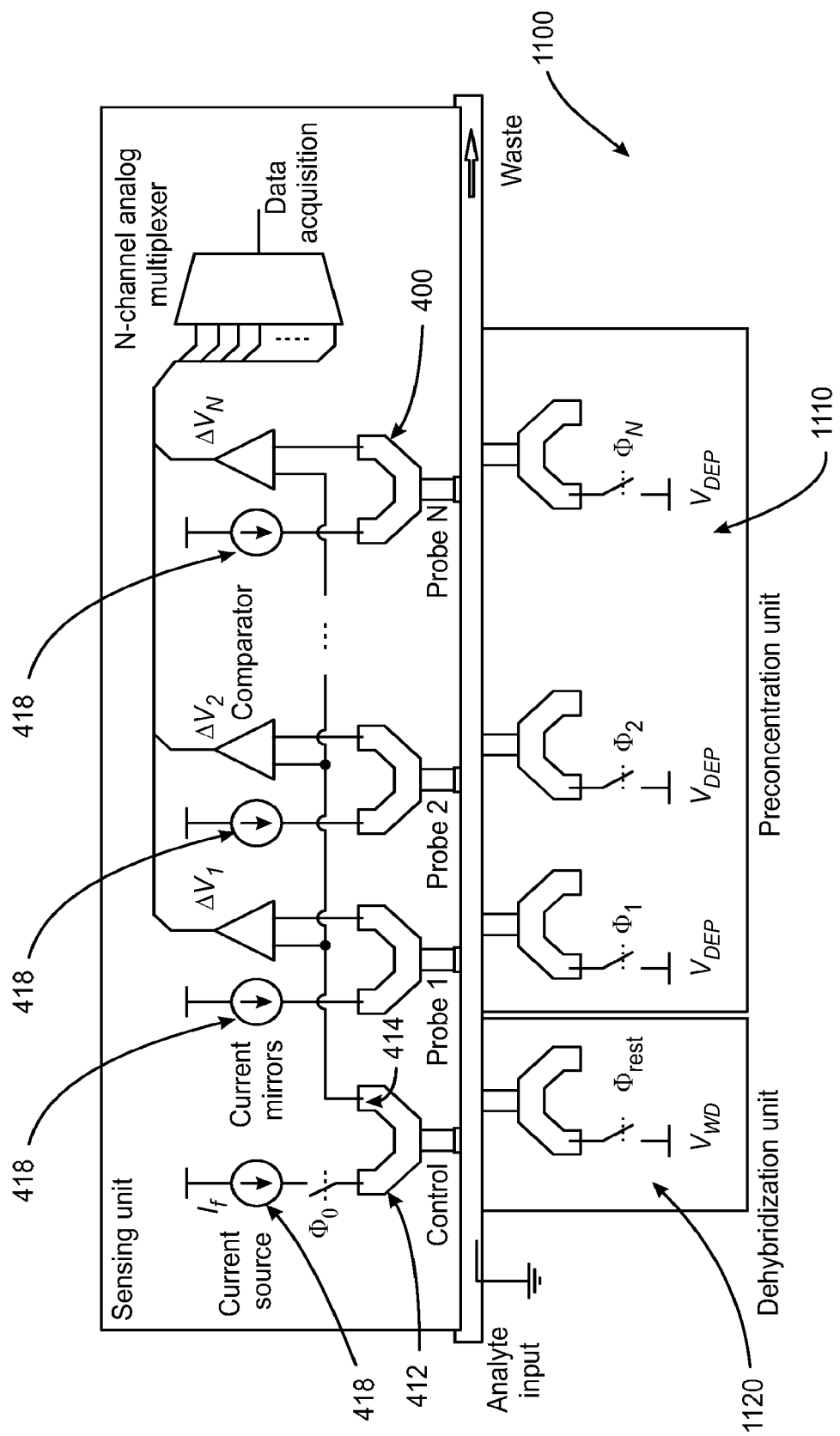
FIG. 11 is an example integrated hybridization sensor in accordance with the teachings of the present disclosure.

An example multi-target unit 1100 is shown in FIG. 11 as a schematic view. The example multi-target unit 1100 generally comprises an integrated smart RNA hybridization sensor composed of a plurality of nanomembrane sensing units, 400, a preconcentration unit 1110, and dehybridization unit 1120. In operation, the unit 1100 offers sequential detection of different targets by moving the sample from one sensor 400 location to the next with the depletion technique. A processor 1140 receives data regarding the sensed hybridization and is able to make a determination regarding the presence and/or lack of target material based upon the sensed data. While the present unit 1100 may be well suited for small sample volumes, for larger volumes, the unit 1100 may be implemented in a parallel design that allows for multiple sample movements.

The Nanoporous membranes disclosed herein can greatly enable and sensitize on-chip molecular sensing. The example disclosed can deplete inhibitors near their surface where the probes are functionalized, such that the platform is robust to a large variety of sample ionic strengths and pH. Still further, the same ion-depletion dynamics extends the Debye layer and hence allows more sensitive conductance and capacitance detection of the hybridized molecules. The high field in the same depletion region can produce fast dielectrophoretic trapping of the larger target molecules. If the depletion region extends across the entire flow channel, it can also trap smaller molecules. Hence, by activating different membrane components on a chip, the molecules can be concentrated and transported to different sensors. The membrane's ability to invert its surface charge upon hybridization produces a large conductance signal for hybridization. A large capacitance signal is also produced, corresponding to the intercept of the Warburg spectrum with the real axis, when the depletion layer is formed periodically under an AC field such that the hybridized target molecules and their counterions are responsible for this asymptotic conductance when all other ions are depleted within the small depletion layer. These nanoporous membranes are fabricated on the chip and are situated on the side of the flowing channel without blocking the flow, such that a high throughput (>1 mL/min) can be achieved. Bipolar nanoporousmembranes can also be used to split water and to exercise precise control of pH near the sensor, to enhance selectivity. This rapid and precise pH control can also allow multitarget sensing with the same probe if the probes are designed to be pH-sensitive.

Figure 12A:
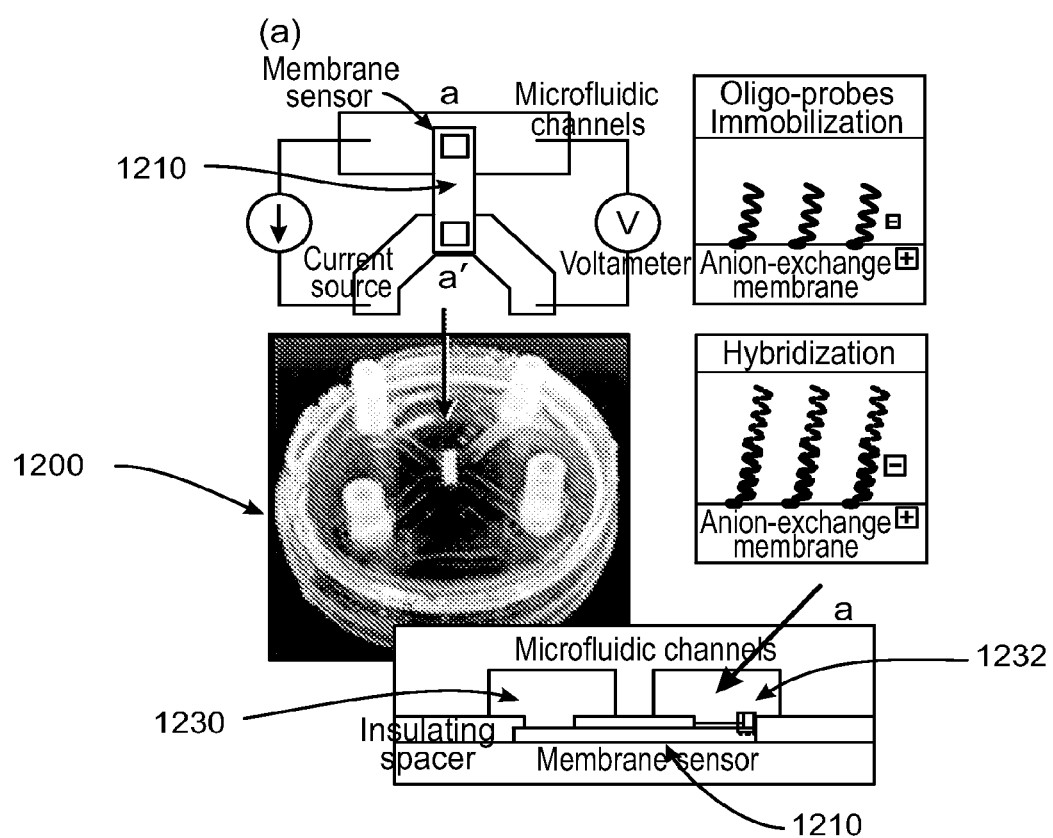
FIGS. 12A-12B together are illustrations of another example device constructed in accordance with the teachings of the present disclosure and showing a graph of the change in characteristics of an I-V plot.

Referring now to FIG. 12A, there is illustrated another schematic representation of a nanomembrane sensing platform 1200 including a single-sensor device 400 in Polydimethylsiloxane (PDMS) with a sensing region 1210 having a dimension of approximately 5 mm×5 mm. In operation, the example sensing platform 1200 utilizes a positively charged anion-exchange membrane 1220 placed to bridge two microchannels 1230, 1232. The example membrane 1220 includes DNA probes (27 nt.) functionalized on one of its openings. As the fluid flows through the microchannels 1230, 1232, the I-V characteristics were measured via Pt electrodes using the previously described circuit, and the processor 1140.

Figure 12B:
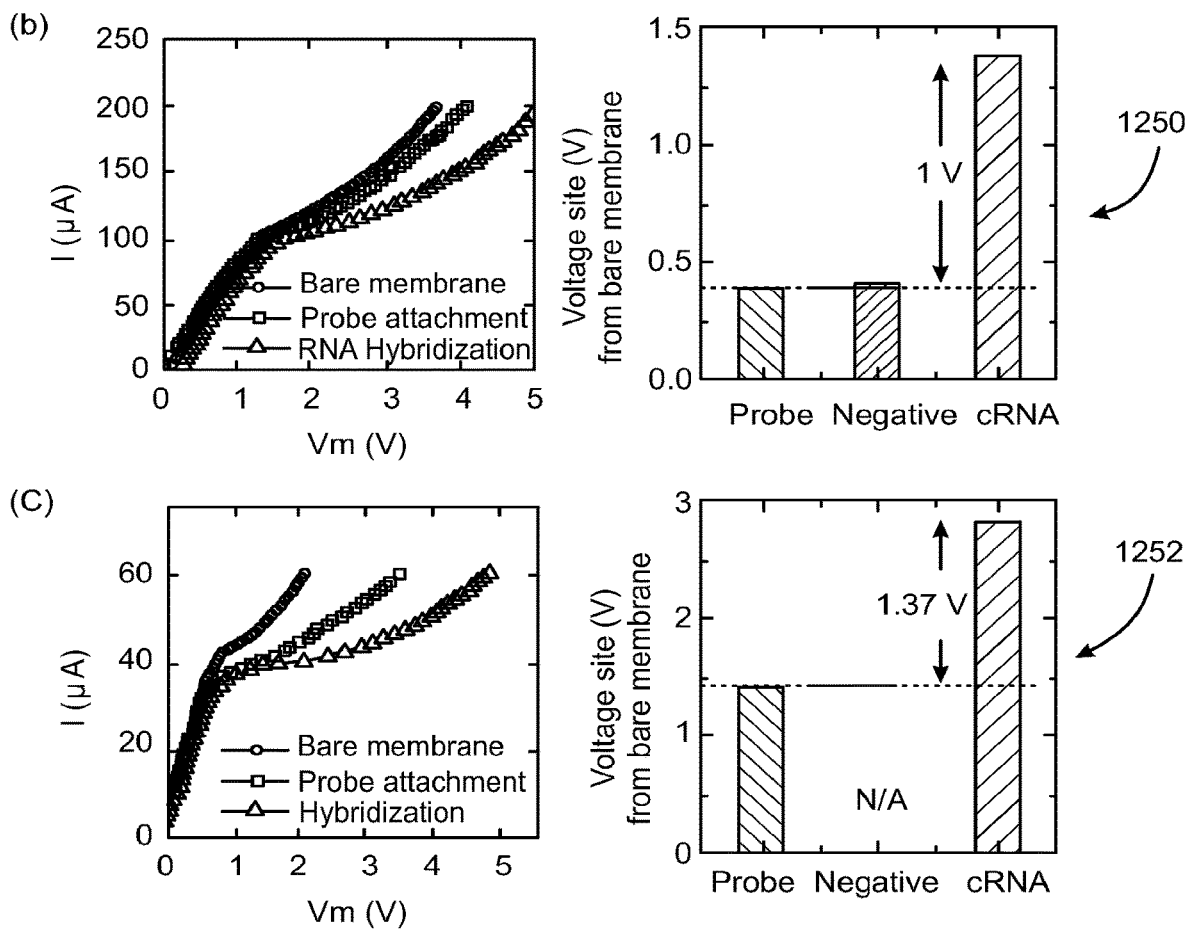

As illustrated in FIG. 12B, a significant change of I-V characteristics in the over limiting-current regime was observed after complementary 10 nM RNA (1250) or 1 nM DNA (1252) hybridization. The 30% to 50% change in conductance is observed compared to typical 5% changes of electrochemical electrode sensors at the same concentration (low-voltage region). With almost no voltage shift for the negative control sample, the sensor exhibits excellent selectivity.

It will be further appreciated by one of ordinary skill in the art that the membrane disclosed herein may be any suitably formed membrane, including a membrane specifically pre-formed and or formed during operation of the device illustrated. For example, the membrane may be formed by the interaction of a nanocolloid, nanostructure, etc, in the microchamber as desired.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A quantitative method for determining a target nucleic acid concentration, the method comprising:
    making an assay mixture containing the target nucleic acid, wherein the target nucleic acid comprises an electrical charge;
    providing a microchamber cell comprising:
        a substrate defining a pair of opposing microchannels; a first pair of opposing electrodes in the opposing microchannels for applying a source signal and a second pair of opposing electrodes for measuring an output signal; and
        at least one ion exchanging nanomembrane having a charge opposite to that of the target nucleic acid coupled between the opposing microchannels such that the opposing microchannels are connected to each other only through the nanomembrane, wherein the nanomembrane is functionalized with a probe complementary to the target nucleic acid wherein the nanomembrane is provided in a nanoslot;
    flowing the assay mixture through one of the microchannels of the microchamber electrochemical cell such that assay mixture contacts the nanomembrane in a manner suitable for hybridization of the assay mixture with the probe, while the other microchannel acts as an auxiliary channel;
    connecting the first pair of opposing electrodes to the device to charge the nanomembrane with the source signal;
    connecting the second pair of opposing electrodes for measuring the output signal across the nanomembrane; and
    detecting a shift to lower resistance in a Warburg impedance spectrum of a nucleic acid solution relative to a control without nucleic acid to determine the concentration of the target nucleic acid.

2. The method of claim 1, wherein a depth of the nanoslot is substantially the same as a depth of the microchannel.

3. The method of claim 1, further comprising providing an AC current across the pair of opposing electrodes.

4. The method of claim 1, wherein the target nucleic acid is at least one of a DNA biomolecule or an RNA biomolecule.

5. The method of claim 1, further comprising deionizing the assay mixture proximate the nanomembrane.

6. The method of claim 1, further comprising bulk-to-membrane ion flux over the depletion region formed by the membrane at over-potentials.

7. The method of claim 1, further comprising forming a non-uniform electroosmotic flow.

8. The method of claim 7, wherein the non-uniform electroosmotic flow leads to microvorticies formed in the fluid flow.

9. The method of claim 7, wherein the non-uniform electroosmotic flow leads to a detectable enhanced ion current.

10. The method of claim 1, further comprising selecting an optimum frequency for each of a particular electrolyte strength wherein the optimum frequency has a sharp minimum in detection time, and wherein the optimum frequency scales as a function of $D/\lambda^2$ where D is a molecular diffusivity of the target nucleic acid and $\lambda$ is the Debye length for the particular electrolyte strength.

* * * * *